United States Patent [19]

Sevastianov et al.

[11] 4,243,043
[45] Jan. 6, 1981

[54] APPARATUS FOR ELECTRICAL STIMULATION OF MAMMAE

[76] Inventors: Viktor V. Sevastianov, ulitsa Komsomolskaya, 96, kv. 31, Ioshkar-Ola; Eduard K. Kazimirov, Brest-Litovsky prospekt, 12, kv. 133, Kiev, both of U.S.S.R.

[21] Appl. No.: 56,516

[22] Filed: Jul. 11, 1979

[51] Int. Cl.³ .............................................. A61N 1/36
[52] U.S. Cl. .................................................. 128/422
[58] Field of Search .......... 128/419 R, 420 R, 421 R, 128/422, 423 R

[56] References Cited

U.S. PATENT DOCUMENTS

| | | | |
|---|---|---|---|
| 3,056,409 | 10/1962 | Edwards | 128/422 |
| 3,589,370 | 6/1971 | McDonald | 128/422 |
| 3,983,881 | 10/1976 | Wickham | 128/422 |
| 4,102,348 | 7/1978 | Hihara et al. | 128/422 |
| 4,140,133 | 2/1979 | Kastrubin et al. | 128/421 |
| 4,177,819 | 12/1979 | Kofski et al. | 128/422 |
| 4,191,188 | 3/1980 | Belt et al. | 128/422 |

Primary Examiner—William E. Kamm
Attorney, Agent, or Firm—Robert E. Burns; Emmanuel J. Lobato; Bruce L. Adams

[57] ABSTRACT

An apparatus for electrical stimulation of the mammae comprises a serial arrangement of a master oscillator, a stimulating pulse generator, an amplitude modulator, a stimulating pulse polarity changing unit, an output unit, and a distributing line with leads for respective points subject to electrical stimulation. In addition, the apparatus comprises modulating signal generator and a unit to form excitation and space periods, which connect each other and the frequency and amplitude modulators as well, and also comprises an automatic stimulating pulse polarity control unit coupled to the stimulating pulse generator, to the modulating signal generator, and to the stimulating pulse polarity changing unit. There is a stimulating pulse amplitude adjustment circuit for each of the points subject to electrical stimulation, coupled to a matching unit which connects surface-type electrodes.

7 Claims, 4 Drawing Figures

APPARATUS FOR ELECTRICAL STIMULATION OF MAMMAE

FIELD OF THE INVENTION

The invention relates to the field of medicine including veterinary medicine and electrical engineering, and more particularly to an apparatus for electrical stimulation of the mammae.

The apparatus of the invention is suitable for use at cattle farms, in specialised hospitals, and in cosmetic rooms.

DESCRIPTION OF THE PRIOR ART

Known in the art are diverse apparatus electrically influencing the organs and tissues of living organisms and applicable to medical uses, including electrical stimulation apparatus producing output signals in the form of continuous or interrupted trains of pulses of a certain shape and length, the parameters of said pulses, for example, amplitude and frequency, being changed according to a given law. There are universal devices of the described type in which the parameters are varied in wide limits and specialised ones which can be used, for example, for electrical stimulation of skeletal muscles and which are given a limited number of parameters. Many firms in various countries, for example, the Disa of Denmark, manufacture such devices.

There are devices for electrical stimulation of living organisms (cf. FRG Pat. Nos. 1,539,722, 1972, 1,589,503, 1973, 2,049,595, 1973, 2,147,704, 1972) in which the polarity of the output signal is varied automatically. After the desirable time has elapsed, the level of the output signal begins to descrease to zero and at the moment when zero is reached the contacts controlling the signal polarity are switched over, with the result that the output signal again rises to a given level. A contact-type clock is used to vary the operating mode of the device within certain time intervals and to change the polarity of the output signal. In such devices, the polarity controlling circuit, including a clockwork and relay contacts, makes it possible to obtain slow switchings of the signal polarity within preset time intervals.

There is an apparatus for generating positive and negative pulses for curing living organisms (cf. U.S. Pat. No. 3,946,745, 1976), which produces a train of double pulses of opposite polarities, said pulses being divided into two groups each of a respective polarity and applied to respective pulse shapers which are connected to an output unit producing the apparatus output signal. In this apparatus, the pulses of opposite polarities are generated in a master oscillator and are given the final shape in the output network, after they have been handled separately in respective polarity forming circuits. The apparatus cannot provide for another law of changing the signal polarity.

Known in the art is an apparatus for pulse stimulation of muscles (cf. French Pat. No. 2,242,996, 1975) comprising a number of units for generating trains of pulses separated by certain intervals, and a number of units performing amplitude modulation of these pulses, with the result that at the beginning of a train the pulse amplitude tends to rise and smooth stimulation is therefore attained at the initial point of treatment. To obtain spaced trains of pulses with smoothly increased amplitude, a sophisticated circuitry of the apparatus is required.

There is a percutaneous stimulator (cf. French Pat. No. 2,183,891, 1974) designed to stimulate certain portions of the subject's body and utilizing an output signal comprised of pulses which include preset frequency components within a given frequency range. This allows for an optimum stimulation of the tactile nerve fibres as distinguished from the pain nerve fibres. In the apparatus, use is made of specific frequency spectra of the output signal so that the living structures of interest are subject to a selective electrical stimulation.

Known in the art is a method of stimulating the milk flow reflex during machine milking (cf. the USSR Inventor's Certificate No. 370,929, 1973). According to the method, the receptors of the nipples of the cow udder are subject to electrical stimulation during milking by using a continuous train of pulses having a given repetition rate. The apparatus carrying out the method produces this train of pulses and effective stimulation of the milk flow reflex is thus attained. Such methods are also used in Great Britain (cf. a collection of review materials entitled "Advanced Milking Systems" by A. N. Khitrov, the VNIITEISKH Institute, Moscow, 1978, p.20).

At present, machine milking of cows used at cattle farms cannot ensure adequate stimulation of the receptors of the mammae, which results in a decreased milk production and increased mastitis rate. To stimulate the mammae receptors, use is made of mechanical massage of manual and other types, and of washing-off of the udder with warm water. Such stimulators cause afferent pulses which produce reflex stimulation of neurohumoral systems and reflex change of the tonus of the smooth muscles of the udder, thereby providing from a considerable increase in the production and quality of milk.

However, this conventional method in which the receptor fields of the mammae are influenced requires considerable physical efforts in the case of mass handling of the animals, which results in poor care, in lesser milk production and in greater mastitis rate. Thus, new methods of influencing the receptor fields of the mammae are needed.

It is known that afferent pulses from the receptors of the mammae can be provoked by stimulating them with electric current which represents, at the preset parameters and dose rates, a universal and most adequate stimulator of nerve and muscle tissues.

The prior art devices dealing with electrical stimulation of the living organs are designed to treat one human being or animal. This imposes economic and technical limitations on the use of such devices for mass handling of animals at cattle farms or human beings in specialised hospitals and cosmetic rooms.

In the case of mass handling of animals, there is a critical problem relating to the possibility of concurrent electrical stimulation of large groups of animals with their individual excitation characteristics being taken into consideration. It is important that each group be comprised of animals having similar physiological conditions such as the pregnacy period of heifers, lactation and interlactation periods, availability or unavailability of symptoms of diseases. In addition, the formation of the groups is dictated by such factors as technological and economical effectiveness of the treatment procedure and the possibility of employment of personnel having no special skills.

To meet the above-mentioned requirements, a respective apparatus must produce an output signal of a flexible structure with which different electrical stimulation techniques can be used for the animal groups of different physiological conditions, the signal being applied to a large group of animals, of 100 to 150 head, so that their individual excitation characteristics are taken into consideration.

A prototype of such an apparatus is not described in the pertinent literature.

SUMMARY OF THE INVENTION

An object of the invention is to provide an apparatus for electrical stimulation of the mammae of human beings or animals subject to concurrent treatment in a group including up to 100 subjects so that their individual excitation characteristics are taken into consideration, said electrical stimulation being applied to groups including subjects having similar physiological conditions, such as animals in the lactation or interlactation period, or heifers, which apparatus provides for higher quantity and quality of milk, for more effective preparation of heifer udders, for proper prevention of diseases, and for normalization of the function of the mamma.

There is provided an apparatus for electrical stimulation of the mammae, comprising, according to the invention, a master oscillator producing a train of pulses, a frequency modulator performing frequency modulation of the pulses produced by the master oscillator and having its input coupled to the output of the master oscillator, a stimulating pulse generator producing pulses of a given length and shape, corresponding to the pulses available from the master oscillator, and having its input coupled to the output of the frequency modulator, an amplitude modulator in which the generated pulse train is subject to amplitude modulation and which has an input coupled to the output of the stimulating pulse generator, a modulating signal generator, a unit adapted to form excitation and space periods, having its input coupled to an output of the modulating signal generator, which is coupled to a control input of the frequency modulator, and having its output coupled to a control input of the amplitude modulator and to another control input of the frequency modulator, a unit adapted to change the polarity of the stimulating pulses according to a given law and having an input coupled to the output of the amplitude modulator, a unit adapted to automatically control the polarity of the stimulating pulses according to the law of changing the polarity, having its output coupled to a control input of the stimulating pulse polarity changing unit, and having its inputs coupled respectively to the output of the stimulating pulse generator and to another output of the modulating signal generator, an output unit comprised of two unipolar signal amplifiers, having a common load, and adapted to produce an output signal with a polarity changed according to the given law, the output unit having its input coupled to the output of the stimulating pulse polarity changing unit, and having its output coupled to a distributing line with leads coupled to respective points subject to electrical stimulation each of the leads being coupled to a stimulation pulse amplitude adjustment circuit which has its output coupled to the input of a matching unit having its output coupled to surface-type electrodes.

It is advantageous that in the apparatus the combination of two unipolar signal amplifiers, the stimulating pulse polarity changing unit and the automatic stimulating pulse polarity control unit are implemented in the form of a circuit including a first preamplifier and a first emitter follower which are provided with an individual supply bus and constitute an amplifier for a signal of a first-type polarity, and also including a second preamplifier and a second emitter follower which are provided with an individual supply bus and constitute an amplifier for a signal of a second-type polarity, the two amplifiers being coupled to a single load, two switch networks and a phase inverter adapted to constitute the stimulating pulse polarity changing unit, the switch networks having their inputs coupled to loads of the phase inverter which is operated to supply the inputs of the switch networks with signals of opposite polarities, and having their outputs coupled to the inputs of the preamplifiers, the phase inverter being coupled to the amplitude modulator, which circuit also includes an RST flip-flop, a matching network built around a transistor which is coupled to an output of the RST flip-flop, a switch unit coupled to the inputs of the RST flip-flop and to a control signal unit and adapted to select the law of changing the polarity of the stimulating pulses, the RST flip-flop, the matching network, the switch unit and the control signal unit being adapted to constitute the automatic stimulating pulse polarity control unit, the output of the matching network and another output of the RST flip-flop being coupled to respective control inputs of the switch networks, and the inputs of the control signal unit being coupled to the output of the stimulating pulse generator and to another output of the modulating signal generator.

It is preferable that in the apparatus the stimulating pulse amplitude adjustment circuit and the matching unit for each of the stimulation areas and the matching unit are built around a circuit including a potentiometer, transistors of opposite conductivities, and diodes, a moving contact of the potentiometer being coupled to the bases of the transistors which have their emitters coupled to an emitter load and have their collectors coupled to the distributing line via the diodes which are connected according to the given polarity of the signal.

It is advantageous that in the apparatus an indication unit is coupled to an indication line having leads for respective points subject to electrical stimulation, said leads being coupled to corresponding pilot lamps and to the output unit to effect visual monitoring of these points and to acknowledge the presence of the apparatus output signal.

The advantages of the apparatus of the invention are as follows: preventing and treatment of mastitis; increased yield and quality of milk; normalization of the tonus of the mammae; reduction of milking time; elimination of hand aftermilking.

The apparatus of the invention is compatible to the conventional methods of treatment of women in hospitals and keeps routine cattle management practice for example, milking procedures. The electrical stimulation can be effected during milking.

In the cases not dealing with milking, use is made of the individual electrodes which are fitted over the nipples of the mammae of animals or over the mammary areolae and upper portions of the mammae of women.

It is possible to handle up to 100 subjects concurrently.

The flexible structure of the output signal allows fulfilment of different aims of stimulation, depending of the physiological condition of the subjects in the given group.

There is a separate signal level regulation for each subject which takes into consideration its individual excitation characteristic.

The apparatus of the invention can be maintained by the personnel having no special skills.

The apparatus of the invention can be used very effectively at large cattle farms where animals are short of natural agent, as the management is affected by the following factors: lock of motion; machine milking: inability to control the quality of care of mammae.

With the apparatus of the invention, an increase in the daily milk-yield amounts to 10 to 15 percent, as compared to that of a control group for which manual massage of the udder is used. The mean yearly milk-yield is equal to 3000–3500 kg. The fat content of milk is increased from 3.3 to 3.6 percent and the milking time is reduced by 1.0–1.5 minutes.

DESCRIPTION OF THE INVENTION

The invention will now be described, by way of example, with reference to the accompanying drawings in which.

Figure 1:
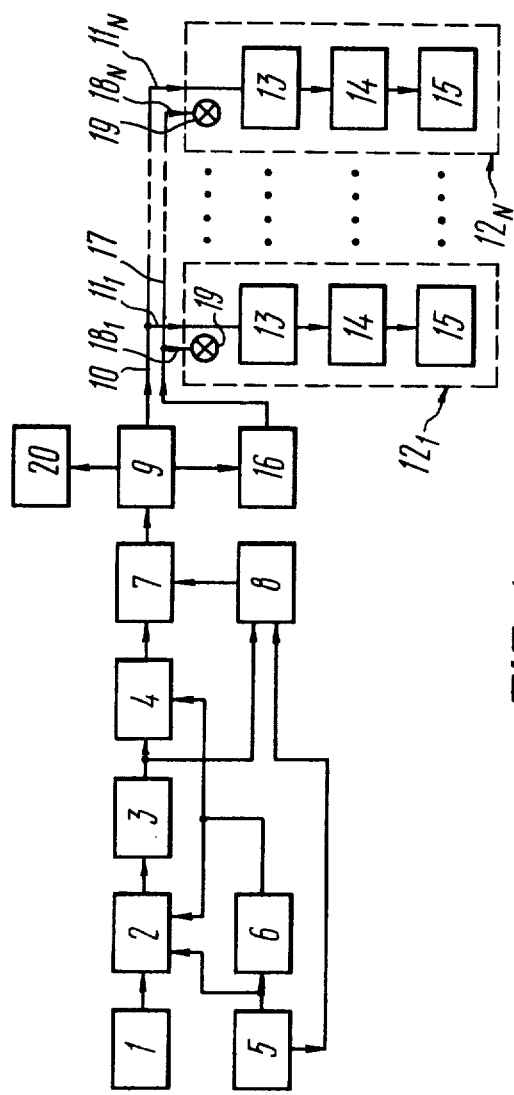
FIG. 1 is a block diagram of an apparatus for electrical stimulation of the mammae, according to the invention.

The apparatus of the invention comprises a master oscillator 1 (FIG. 1) producing a train of pulses, a frequency modulator 2 designed to perform frequency modulation of these pulses and having its input coupled to the output of the master oscillator 1, a stimulating pulse generator 3 which produces pulses of a given length and shape, corresponding to the pulses available from the master oscillator 1, and has its input coupled to the output of the frequency modulator 2.

An amplitude modulator 4 is used to perform amplitude modulation of the generated train of pulses and has its input coupled to the output of the stimulating pulse generator 3. The apparatus also comprises a modulating signal generator 5 and a unit 6 adapted to form excitation and space periods and having its input coupled to an output of the modulating signal generator 5, which is coupled to a control input of the frequency modulator 2. The output of the unit 6 is coupled to a control input of the amplitude modulator 4 and to another control input of the frequency modulator 2.

There is a unit 7 adapted to change the polarity of the stimulating pulses and having its input coupled to the output of the amplitude modulator 4. The apparatus also comprises a unit 8 adapted to automatically control the polarity of the stimulating pulses and having its output coupled to a control input of the unit 7, and also having its inputs coupled to the output of the stimulating pulse generator 3 and to another output of the modulating signal generator 5.

An output unit 9 has its input coupled to the output of the unit 7 and has its output coupled to a distributing line 10 with leads $11_1, \ldots, 11_N$ coupled to respective points $12_1, \ldots 12_N$ subject to electrical stimulation.

Each of the leads $11_1, \ldots, 11_N$ is coupled to a stimulating pulse amplitude adjustment circuit 13 which has its output coupled to a matching unit 14. Coupled to the output of the matching unit 14 are surface-type electrodes 15 which are fixed to the subject under treatment (not shown).

The apparatus comprises an indication unit 16 having its input coupled to the output of the output unit 9, and having its output coupled to an indication line 17 with leads $18_1, \ldots, 18_N$ for respective points $12_1, \ldots, 12_N$ subject to electrical stimulation. Coupled to the leads $18_1, \ldots, 18_N$ are respective pilot lamps 19. A measuring unit 20 has its input coupled to the output of the output unit 9.

The output unit 9 is a combination of two unipolar signal amplifiers having a common load 21 (FIG. 2) and producing an output signal whose polarity varies in accordance with a given law.

The amplifier producing a first-type polarity comprises a preamplifier 22 and an emitter follower 23 having an individual supply bus 24.

The amplifier producing a second-type polarity signal comprises a preamplifier 25 and an emitter follower 26 having an individual supply bus 27.

The stimulating pulse polarity changing unit 7 comprises two switch networks 28, 29 and a phase inverter built around a transistor 30 and having loads 31, 32. The switch networks 28, 29 are coupled respectively to the loads 31, 32 and to the preamplifiers 22, 25. The base of the transistor 30 is coupled to the output of the amplitude modulator 4.

The automatic stimulating pulse polarity control unit 8 comprises an RST flip-flop 33, a matching network built around a transistor 34 having a load 35 and coupled to an output of the RST flip-flop 33, and a switch unit 36 coupled to the inputs of the RST flip-flop 33 and to a control signal unit 37 so as to select the law of changing the polarity of stimulating pulses.

The load 35 of the matching network and the other output of the RST flip-flop 33 are coupled to the control inputs of the switch networks 28, 29, respectively.

The inputs of the control signal unit 37 are coupled to the stimulating pulse generator 3 and to another output of the modulating signal generator 5.

The stimulating pulse amplitude adjustment circuit 13 designed to adjust the amplitude of the stimulating pulses at the points $12, \ldots, 12$ subject to electrical stimulation is implemented in the form of a potentiometer 38.

The matching unit 14 comprises transistors 39, 40 of opposite conductivities, diodes 41, 42, and an emitter load 43.

A moving contact of the potentiometer 38 is coupled to the bases of the transistors 39, 40 having their emitters coupled to the emitter load 43, and having their collectors coupled to the distributing line 10 via the diodes 41, 42. Coupled to the distributing line 10 is the anode of the diode 41 and the cathode of the diode 42.

Figure 3:
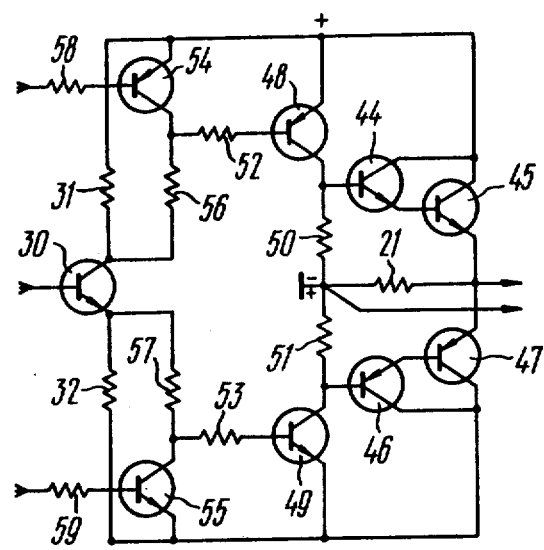
FIG. 3 is a circuit diagram of an output unit and a stimulating pulse polarity changing unit, according to the invention.

FIG. 3 illustrate modifications of the output unit 9 and the stimulating pulse polarity changing unit 7.

The emitter followers 23, 26 (FIG. 2) employ combination transistors 44 (FIG. 3), 45, 46, 47, respectively. The preamplifiers 22 (FIG. 2), 25 employ transistors 48 (FIG. 3), 49 with loads 50, 51 and base resistors 52, 53, respectively.

The switch networks 28 (FIG. 2), 29 employ transistors 54 (FIG. 3), 55 with loads 56, 57 and base resistors 58, 59, respectively.

Figure 4:
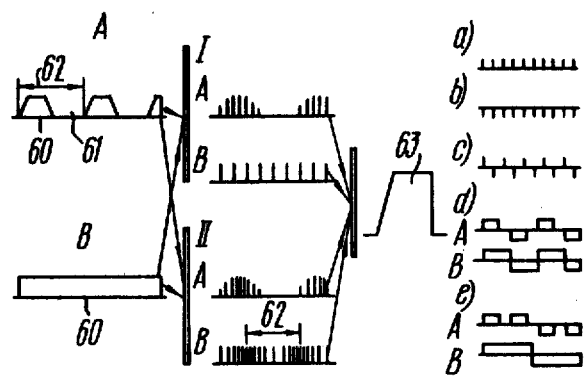
FIG. 4 shows timing diagrams of the output signal, according to the invention.

FIG. 4 illustrates timing diagrams for the output signal.

The apparatus of the invention operates on the principle that a pulsed electrical signal applied to the receptor fields of the mammae via surface-type electrodes makes these receptor fields excited. The afferent pulses so produced provide for normalization and stimulation of the physiological functions of the organism of the subject, either human being or animal through the reflex effect.

FIG. 1 illustrates a block diagram of the apparatus of the invention. The master oscillator 1 produces a continuous train of pulses of a given polarity and repetition rate. The master oscillator 1 is built around a unijunction transistor. The pulse repetition rate is determined by the time within which a capacitor (not shown) is charged. The desirable frequency range is selected by switching the capacitors of different ratings.

The capacitor is charged via a transistor used as a controlled ressistor. This transistor constitutes together with a control circuit the frequency modulator 2. There are two operating modes as follows: the constant frequency mode in which the desirable frequency is selected manually by operating a knob, and the frequency modulation mode in which the frequency is varied automatically within the selected frequency ranges such as 4 to 20 Hz, 20 to 100 Hz, and 100 to 500 Hz.

The signal produced by the frequency modulator 2 is applied to the stimulating pulse generator 3 which generates, for each pulse available from the master oscillator 1, a stimulating pulse of a given length, for example, from 0.2 to 25 ms, and of a given width of the leading edge of the pulse, for example, from 0.1 to 0.5 ms.

The stimulating pulse generator 3 is a driven multivibrator. The forming stage for the leading edge of the pulse comprises a capacitor whose charge time constant determines the width of the leading edge.

Thus, the master oscillator 1, the frequency modulator 2 and the stimulating pulse generator 3 produce a continuous sequence of unipolar pulses with a given length and with a given width of the pulse leading edge. These pulses having a constant or a modulated frequency are applied to the input of the amplitude modulator 4.

The modulating signal to modulate the frequency and amplitude is generated by the modulating signal generator 5 whose output produces a continuous signal whose waveform is represented by equilateral triangles. The length of the latter selected, for example, from 1 to 30 seconds determines the duration of the subject excitation cycle. The triangularwave signal is obtained by means of conventional capacitor charging discharging circuits in which square-wave pulses are applied to the stage where charging (discharging) is accomplished.

Square-wave pulses are applied to the automatic stimulating pulse polarity control unit 8 and are used as markers to acknowledge the termination of the cycle. A triangular-wave signal is applied to an input of the frequency modulator 2 and is used in one of the frequency modulation modes. That signal is subject for further processing in the unit 6 adapted to form excitation and space periods. The unit 6 operates to perform downward clipping of the triangular-wave signal and its output produces a signal in the form of equilateral triangles spaced by intervals with zero signal. When the unit 6 produces a signal the excitation period takes place; when the signal is not present this means that a space period is available. By adjusting the clipping level of the signal, various relationships between the excitation and space periods within the same cycle, for example, from 1:1 to 1:3, can be obtained. The output signal of the unit 6 is applied to the amplitude modulator 4 and to the frequency modulator 2.

The amplitude modulator 4 is a voltage divider with an adjustable resistor from which the modulated signal is picked up. The adjustable resistor is a transistor operated in a manner that the modulating signal, represented by equilateral triangle-wave pulses, is subject to upward clipping and the envelope of the modulated signal is a trapezoid in which the signal rises and drops, respectively, at the beginning and end of the excitation period. The amplitude modulator 4 operates to control the signal level.

The components labelled by reference numerals 1, 2, 3, 4, 5, 6 operate to determine the signal structure as shown in FIG. 4.

Produced at the output of the amplitude modulator 4 (FIG. 1) is the signal A (FIG. 4) with alternating excitation periods 60 and space periods 61 which constitute an axcitation cycle 62. The lengths of the excitation cycle and the excitation and space periods are determined by the shape of the modulating signal. When no modulating signal is applied to the amplitude modulator 4, the continuous excitation mode characterized by the signal B is provided.

The excitation periods 60 are represented by a train of pulses 63 whose repetition rate is formed in the frequency modulator 2 (FIG. 1). When no modulating signal is present, the pulse repetition rate is held constant and the mode I (FIG. 4) is selected in the master oscillator 1 (FIG. 1).

In the case of frequency modulation (the mode II, FIG. 4), the modulating signal for the signal A is the output signal of the unit 6 (FIG. 1) in the form of equilateral triangles space by intervals. In this case, higher frequency corresponds to higher signal level. Since the same signal is used for amplitude modulation, there results a synchronous amplitude-frequency modulation with a frequency maximum at the center of the excitation period. In the case of the signal B (FIG. 4), the modulating signal is a triangular-wave signal obtainable from the output of the modulating signal generator 5 (FIG. 1).

In the units 7 and 8, the polarity if the signal is formed but its parameters are not changed. The laws according to which the signal polarity is changed are illustrated by FIGS. 4a, b, c, d, e. FIGS. 4a, b show the signals of positive and negative polarities, respectively. Shown in FIG. 4c is a signal whose polarity is changed every other pulse, while the signals shown in FIGS. 4d, e have their polarities changed every other cycle and after a certain time interval, respectively.

The output unit 9 (FIG. 1) operates to increase the signal power and to provide for matching the apparatus output with the distributing line 10 whose leads $11_1, \ldots, 11_N$ are used to deliver the signal to respective points $12_1, \ldots, 12_N$ subject to electrical stimulation.

Thus, a group of N subjects, human beings or animals, is handled on a mass basis, N being equal, for example, to 100.

The stimulating pulse amplitude adjustment circuit 13 is operated to select the signal level required for the given subject, said signal being applied, via the matching unit 14, to the surface-type electrodes 15. The individual excitation characteristics of the subjects are therefore taken into consideration.

The indication unit 16 provides for convenient operation of the apparatus of the invention. The unit 16 comprises an individual power supply which connects, via an adjustable reactor in the form of a transistor, the indication line 17. The latter has the leads $18_1, \ldots, 18_N$ coupled to the pilot lamps 19 for respective points $12_1, \ldots, 12_N$ subject to electrical stimulation. Applied to the control input of the adjustable resistor (not shown) is the signal from the output unit 9. With the apparatus energized and the signal unavailable, the pilot lamps give off a preset level of brilliance. When the signal is present, the brilliance is changed according to the signal amplitude in synchronism with the excitation period. Thus, one can monitor the energization of the apparatus and the presence of the signal passing through the distributing line 10 to respective points $12_1, \ldots, 12_N$ subject to electrical stimulation.

The measuring unit 20 is used to measure and indicate the amplitude of the output signal.

Figure 2:
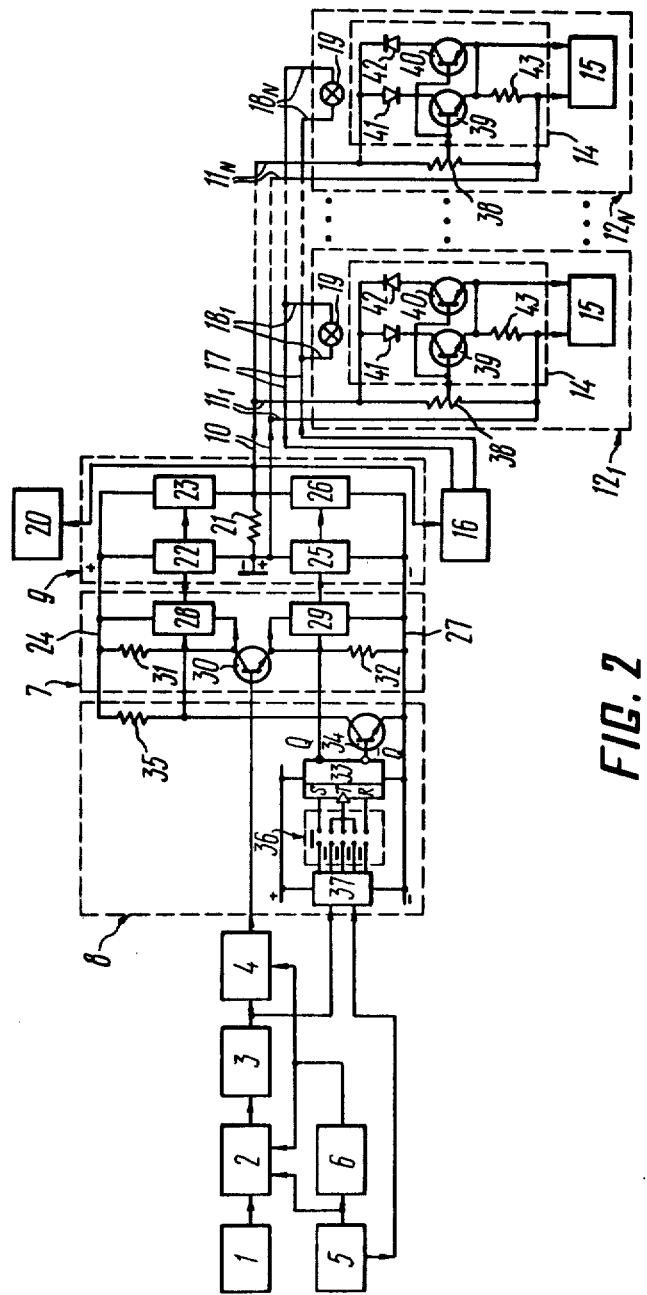
FIG. 2 is a functional diagram of the apparatus for electrical stimulation of the mammae, according to the invention.

FIG. 2 illustrates in greater detail the components 7,8,9,13,14 which constitute the output circuits of the apparatus.

The circuitries of the units 7, 8 are chosen in accordance with the type of the output unit 9.

The output unit 9 comprises two independent unipolar signal amplifiers working into the common load 21.

The first and second amplifiers provide, respectively, the signals of positive and negative polarity. The positive signal is obtained from the first amplifier comprising the preamplifier 22 and the output emitter follower 23 with the load 21. This stage takes power from the individual supply bus 24.

The negative signal is provided by the second amplifier fed from the individual supply bus 27 and comprising the preamplifier 25 and the output emitter follower 26 which is connected to the load 21. The output signal of the amplitude modulator 4 has the same polarity and passes to the unit 7, namely, to the input of the phase inverter built around the transistor 30 with equal collector-emitter loads 31, 32. The latter produce signals of equal magnitude and opposite polarity, as related to the buses 24, 27; this means that the load 31 produces a negative signal as related to the bus 24, while the load 32 produces a positive signal as related to the bus 27. These signals are input ones for respective amplifiers and are applied to the inputs of the preamplifiers 22, 25 via the switch networks 28, 29, respectively.

The input of the respective preamplifier 20 or 25 receives the signal only when the respective switch network 28 or 29 is conducting, and the load 21 produces a respective signal under these conditions only. At a given point in time, only one of the switch networks 28, 29 is conducting, only one amplifier of the output unit 9 is operative and the output of the latter produces a signal of a given polarity. Holding the switch networks 28, 29 in the required states enables output signals of different polarities and various sequences to be generated. The switching of the switch networks 28, 29 is accomplished within the space periods between the pulses or within the spaces between the excitation periods.

The automatic stimulating pulse polarity control unit 8 is used to control the state of the switch networks 28, 29. The main subassembly of the unit 8 is the RST flip-flop 33. The $\overline{Q}$ output of the RST flip-flop 33 controls the operation of the switch network 28, while the Q output of the flip-flop controls the operation of the switch network 29. To obtain the control signal for controlling the state of the switch network 28 with respect to the bus 24, the $\overline{Q}$ output of the RST flip-flop 33 is coupled to the matching network built around the transistor 34 whose load 35 produces that control signal. The matching network does not provide for the inverting of the signal.

The state of the RST flip-flop 33 is determined by input signals applied thereto. FIG. 2 illustrates a modification of a connection diagram for the RST flip-flop 33. At each point in time, one pair of the contacts of the switch unit 36 are closed. When the latter operates to connect the S or R input of the RST flip-flop 33 to the control signal unit 37, the flip-flop goes to the corresponding state which determines the positive or negative polarity of the signal. The RST flip-flop 33 automatically changes its state, with the result that the polarity of the output signal is changed, when its complement input (labelled T) is activated. The control pulses from the output of the control signal unit 37 are applied to the T input of the flip-flop and the polarity is changed when the signal is not present, namely, within the spaces between the pulses or between the excitation periods. This condition is attained by generating in the control signal unit 37 the signals for controlling the operation of the RST flip-flop 33. To keep the flip-flop in a state determined by the S or R input thereof, the corresponding input is coupled to the zero supply bus of the flip-flop. The control pulses are formed which control the state of the RST flip-flop 33 related to the T input. Received by the input of the control signal unit 37 are the stimulating pulses from the stimulating pulse generator 3 and the pulses from one of the outputs of the modulating signal generator, 5, which are used to acknowledge that the given cycle is terminated. In the operating mode dealing with switching the polarity every other pulse, the control pulses are formed at the moment coinciding with the trailing edge of the stimulating pulses.

When the polarity is switched over every other cycle, the control pulses are formed at the moment coinciding with the trailing edge of the cycle termination pulses, in the middle of the space between the excitation periods. When a stimulating signal with continuous excitation is used, the polarity is switched over at the moment when two events coincide, namely, the termination of the cycle and the termination of the present stimulating pulse.

To switch over the polarity after a certain time interval has elapsed, for example, after 1- to 5-min. time interval, the electronic timer of the control signal unit 37 generates pulses after a given time interval. The polarity of the output signal is switched over when two events concide, namely, the termination of the given time interval and the termination of either the cycle or the present pulse, according to the signal A or B (FIG. 4).

FIG. 3 illustrates a modification of the output unit 9 in which the amplifier for the positive polarity signal utilizes the transistors 44, 45, 48.

The input signal available from the load 31 of the phase inverter passes through the resistors 56, 52 when the transistor 54 of the switch network is not conducting. In this case, logic Q is present at the $\overline{Q}$ output of the RST flip-flop 33 (FIG. 2). When the transistor 54 (FIG. 3) reaches its saturation state, no signal is applied to the input of the preamplifier.

The final stage for the negative polarity signal utilizes a similar circuitry, but the transistors 46, 47, 49 have the opposite polarity and the switch network employs the transistor 55.

The advantages of the output unit 9 are that zero balance is not needed, the d.c. component at the output is not present when zero signal is available, a very important feature in the apparatus influencing living organisms, and the amplifier takes no power when the signal is not present.

The stimulating pulse available from the load 21 (FIG. 2) of the output unit 9 passes to the distributing line 10 having its leads $11_1, \ldots, 11_N$ connected to the subjects being stimulated. Proper connection of a subject to the distributing line 10 must meet the following requirements: when the signal amplitude is adjusted at each of the points $12_1, \ldots, 12_N$ subject to electrical stimulation, the signal shape, and especially the width of the pulse leading edge, should not vary; within the entire adjustment range at N points of electrical stimulation, the amplitude of the stimulating pulse along the distributing line 10 should not vary; and the potentiometers 38 should not provide for a marked increase in the power consumed. In the circuit described by FIG. 2, these requirements are met.

The stimulating pulse amplitude adjustment circuit 13 (FIG. 1) is the potentiometer 38 (FIG. 2) whose rating is several times (for example, 5) that of the load (subject), and an extra power consumption does not exceed 20 percent in this case. The matching unit 14 comprises the transistors 39, 40 of the opposite conductivites, diodes 41, 42 and emitter load 43. The circuitry includes two stages which behave like emitter followers with a common load. In the case of the output signal of positive polarity, the diode 41 is conducting and the stage built around the transistor 39 is operative. The diode 42 is not conducting, the collector of the transistor 40 is separated from the distributing line 10, and the polarity of the signal across the potentiometer 38 is such that the base-emitter junction of the transistor 10 is not conducting; in other words, the circuitry of the transistor 40 do not influence the operating stage.

After the polarity of the output signal has been changed, the diode 42 is made conducting and the signal is applied to the load (subject) when passing through the stage built around the transistor 40. The low output impedance of the stage provides for a small time constant for the charging process in the load capacitor. As a result, a change of the width of the leading edge is within permissible limits for the entire range of adjusting the signal level.

The proper selection of the signal structure and the law according to which the signal polarity is changed makes it possible to create an adequate stimulation effect for groups of human beings or animals in various physiological conditions.

A flexible signal structure and the preset parameter adjustment range provide for electrical stimulation of various character such as an intense excitation of the receptor fields of the mamma, a normalizing action, or a curing action in the case of a pathological process.

There are contraindications of general nature and relating to cases where the application of a pulsed electric current is impracticable. They include epilepsy, frequently encountered spasms, benignant and malignant tumors of the mamma, and skin diseases of the mamma.

The apparatus of the invention therefore allows for mass handling of human beings or animals without an increase in the personnel requirements and without greater costs. The apparatus of the invention is especially suitable for large cattle farms and specialised hospitals. The use of the apparatus provides for a decrease in management and curing costs related to animals and human beings, for an increase in milk production at cattle farms, and for better physiological condition of the animals being handled.

What is claimed is:

1. An apparatus for electrical stimulation of the mammae, comprising:

a master oscillator producing a train of pulses, having an output;

a frequency modulator adapted to perform frequency modulation of the pulses generated by said master oscillator and having an input, control inputs, and an output, said input being coupled to said output of said master oscillator;

a stimulating pulse generator producing pulses of a given length and shape, corresponding to respective pulses obtainable from said master oscillator; an input and an output of said stimulating pulse generator, said input being coupled to said output of said frequency modulator;

an amplitude modulator in which said generated train of pulses is subject to amplitude modulation; an input, a control input and an output of said amplitude modulator, said input being coupled to said output of said stimulating pulse generator;

a modulating signal generator having outputs;

a unit adapted to form excitation and space periods and having an input and an output, said input being coupled to a first one of said outputs of said modulating signal generator, which is coupled to a first one of said control inputs of said frequency modulator, and said output of said forming unit being coupled to said control input of said amplitude modulator and to a second one of said control inputs of said frequency modulator;

a stimulating pulse polarity changing unit adapted to change the polarity of the stimulating pulses according to a given law, said unit having an input, a control input and an output, said input being coupled to said output of said amplitude modulator;

an output unit comprised of a combination of two unipolar signal amplifier, which have a common load, said output unit being adapted to produce an output signal with its polarity changed according to a given law, and having an input and an output, said input being coupled to said output of said stimulating pulse polarity changing unit;

a distributing line relating to N points subject to electrical stimulation and having leads connected to each of said N points;

an automatic stimulating pulse polarity control unit operated to realize a given law of changing the polarity of the output signal and having inputs and an output, said output being coupled to said control input of said stimulating pulse polarity changing unit, and said inputs being coupled to said output of said stimulating pulse generator and to said second output of said modulating signal generator, respectively;

said output of said output unit coupled to said distributing line;

a stimulating pulse amplitude adjustment circuit having an input and an output and designed for each of said points subject to electrical stimulation;

a matching unit having an input and an output;

surface-type electrodes;

said input of said stimulating pulse amplitude adjustment circuit, coupled to a respective lead, and said output of said stimulating pulse amplitude adjustment circuit, coupled to said input of said matching unit;

said output of said matching unit, coupled to said surface-type electrodes.

2. An apparatus as claimed in claim 1, wherein said combination of two unipolar signal amplifiers, said stimulating pulse polarity changing unit and said automatic stimulating pulse control unit are implemented in the form of a circuit comprising:

a load;

a first preamplifier;

a first emitter follower coupled to said first preamplifier;

a first individual supply bus to feed said first preamplifier and emitter follower;

said first preamplifier, emitter follower and individual supply bus adapted to constitute an amplifier for a signal of a first-type polarity;

a second preamplifier;

a second emitter follower coupled to said second preamplifier;

a second individual supply bus to feed said second preamplifier and emitter follower;

said second preamplifier, emitter follower and individual supply bus adapted to constitute an amplifier for a signal of a second-type polarity;

said amplifiers for said first- and second-type polarities, coupled to said load;

two switch networks having inputs, control inputs, and outputs;

a phase inverter adapted to apply to said inputs of said switch networks signals of opposite polarities and coupled to said amplitude modulator;

loads of said phase inverter;

said inputs of said switch networks, coupled to said loads of said phase inverter;

said outputs of said switch networks, coupled to said inputs of said preamplifiers;

said switch networks and phase inverter adapted to constitute said stimulating pulse polarity changing unit;

an RST flip-flop having inputs and outputs;

a matching network built around a transistor which is coupled to one of said outputs of said RST flip-flop;

a control signal unit;

a switch unit coupled to said inputs of said RST flip-flop and to said control signal unit and adapted to select the laws according which the polarity of the stimulating pulses is changed;

an output of said matching network and the other output of said RST flip-flop, coupled to respective control inputs of said switch networks;

inputs of said control signal unit, coupled to said output of said terminating pulse generator and to the other output of the modulating signal generator;

said RST flip-flop, matching network, switch unit and control signal unit adapted to constitute said automatic stimulating pulse polarity control unit.

3. An apparatus as claimed in claim 1, wherein said stimulating pulse amplitude adjustment circuit for each of said points subject to electrical stimulation and said matching unit are implemented in the form of a circuit comprising:

a potentiometer;

two transistors of opposite conductivities;

two diodes;

an emitter load;

a moving contact of said potentiometer, coupled to the bases of said transistors which have their emitters coupled to said emitter load;

collectors of said transistors, coupled to said distributing line via said diodes which are connected according to the given polarity of the signal.

4. An apparatus as claimed in claim 1, comprising an indication unit coupled to said output unit to provide for visual monitoring of the points subject to electrical stimulation and to acknowledge the presence of the apparatus output signal.

5. An apparatus as claimed in claim 2, wherein said stimulating pulse amplitude adjustment circuit for each of said points subject to electrical stimulation and said matching unit are implemented in the form of a circuit comprising:

a potentiometer;

two transistors of opposite conductivities;

two diodes;

an emitter load;

a moving contact of said potentiometer, coupled to the bases of said transistors which have their emitters coupled to said emitter load;

collectors of said transistors, coupled to said distributing line via said diodes which are connected according to the given polarity of the signal.

6. An apparatus as claimed in claim 2, comprising:

an indication line with leads for respective points subject to electrical stimulation, each of said leads being coupled to a pilot lamp;

an indication unit coupled to said indication line and to said output unit to effect visual monitoring of the points subject to electrical stimulation and to acknowledge the presence of the appratus output signal.

7. An apparatus as claimed in claim 3, comprising:

an indication line with leads for respective points subject to electrical stimulation, each of said leads being coupled to a pilot lamp;

an indication unit coupled to said indication line and to said output unit to effect visual monitoring of the points subject to electrical stimulation and to acknowledge the presence of the apparatus output signal.

* * * * *